US006326001B1

(12) United States Patent
Inzana et al.

(10) Patent No.: US 6,326,001 B1
(45) Date of Patent: *Dec. 4, 2001

(54) RECOMBINANT VACCINE FOR DISEASES CAUSED BY ENCAPSULATED ORGANISMS

(75) Inventors: Thomas J. Inzana, Blacksburg, VA (US); Christine Ward, Irving, TX (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/115,824

(22) Filed: Jul. 15, 1998

Related U.S. Application Data (63) Continuation of application No. 08/673,814, filed on Jun. 27, 1996.

(51) Int. Cl.[7] .......................... A01N 63/00; C12N 15/00; C12N 15/74; C12N 1/20
(52) U.S. Cl. .................. 424/93.4; 424/93.2; 435/440; 435/471; 435/252.3
(58) Field of Search ................... 424/93.1–2, 184, 424/93.46; 514/44; 435/440, 471, 252.1, 252.3

(56) References Cited

U.S. PATENT DOCUMENTS 5,429,818 * 7/1995 Inzana ............................... 424/256.1

FOREIGN PATENT DOCUMENTS

WO9310815 * 6/1993 (WO).

OTHER PUBLICATIONS

Benjamini, Immunology: A short course, Wiley–Liss, pp. 4–5, 1991.*
Webster's New World Dictionary, immunity, p. 675, 1991.*

* cited by examiner

Primary Examiner—Christine J. Saoud
Assistant Examiner—Sharon Turner
(74) Attorney, Agent, or Firm—McGuireWoods LLP (57) ABSTRACT

Vaccines for diseases caused by normally encapsulated organisms are produced by genetically modifying those organisms by deleting the genes encoding for capsule synthesis or a portion thereof sufficient to produce non-capsulated mutants of the organisms. As an example, a live, attenuated strain of *Actinobacillus pleuropneumoniae* genetically modified with a large deletion in a chromosomal regions of the DNA which encodes for capsule synthesis is a safe and effective vaccine against swine pleuropneumonia.

5 Claims, 10 Drawing Sheets

```
AAGCTTGAGCAGGCAGCCAAACTAGCAACCAGCCCCAAAGAAAGGAGTAATCTAAGTTTGATGAGTTTCATCTAATTTCTCTTCAATATATTAAGGAATAACAAC    105

TATATAGGTATGTCTTAAAATCCACATAAAGATTGATTTTAATAAGTTACCTAATCAAGAGAAATTAAATATAAGAAATTTACAAACAAATTAAAAATGTATTT    210

-35
TTTTTAAAAAAAAGTAAATCAAGAGGGGCGTTATACAGATAAACATTATAATTTAAAAGCCATATAAAATACGGAGTTTCCCCTAGATAGTTGATAAATTTCTCA    315

-10
TTTATATTTATGAAATTCCGATGAAAAATTTATCAACTATCTAGGGTAACTCCATAACGTATTCGTATTTCAGGAGTATTTTTAATGTCTAGCATAATGACTCGT    420
                                                                    CpsA →   M  S  S  I  M  T  R
                                                                                  P  I  I  N  H  V  M  S  R  D  I  Q  S  G  I  F  S  S  I  L  E  Y  F  T  D  F  G  S  N  E  F  Q  H  I  V
CCTATAATTAATCATGTAATGTCTAGAGATATTCAAAGTGGCATATTTAGTTCTATTTTAGAATATTTTACTGATTTTGGTTCCAATGAATTTCAACATATTGTC    525

P  I  I  N  H  V  M  S  R  D  I  Q  S  G  I  F  S  S  I  L  E  Y  F  T  D  F  G  S  N  E  F  Q  H  I  V
AGTGTATCTCCAATACCTGAAGCTAAAGTTTATCACTATCACCGTCCACACCTAGAAGAAAAATTATTACCTAATTCTGTTTGTACAGTACATCATGACCTCAAT    630

S  V  S  P  I  P  E  A  K  V  Y  H  Y  H  R  P  H  L  E  E  K  L  L  P  N  S  V  C  T  V  H  H  D  L  N
GATCCAGATCCTTGGCATGCTAAGTATAGATTTATTCCTAGATATATGGAAGCTGGGGCTATAATTTGTTTAAATTACACTCAAAAAGAAATTTTAATATCTCAG    735

D  P  D  P  W  H  A  K  Y  R  F  I  P  R  Y  M  E  A  G  A  I  I  C  L  N  Y  T  Q  K  E  I  L  I  S  Q
GGACTTCCGGAACATAAGTTATTTGTGATTCCTCACGGATATAATCAAAAAGTATTATTTCCTAAGAAAATTAAAGAAATATCAAGTACAGATAAAATTACCTTA    840

G  L  P  E  H  K  L  F  V  I  P  H  G  Y  N  Q  K  V  L  F  P  K  K  I  K  E  I  S  S  T  D  K  I  T  L
GGAATTGCTTCACGGAGATATGGTAGAAGAGTAAAAGGAGATGCATATTTATTTGAATTAGCAAAAAGATTAAATCCAGACCATTTTAAATTTATTTTTGTTGGT    945

G  I  A  S  R  R  Y  G  R  R  V  K  G  D  A  Y  L  F  E  L  A  K  R  L  N  P  D  H  F  K  F  I  F  V  G
AAAGATAGACAATATAGTGCCTTAGAAATGCAAGATCTAGGATTTGAAGCTCAAGTATATGAAAGATTGCCATATAGAATGTTTCAAAGTTTTTATAATAATATT    1050

K  D  R  Q  Y  S  A  L  E  M  Q  D  L  G  F  E  A  Q  V  Y  E  R  L  P  Y  R  M  F  Q  S  F  Y  N  N  I
GATGTACTACTTATGTGTAGTAGTCATGAAGGTGGACCTGCAAATATCCCCGAAGCATTAGCTACTGGGACACCTATATTTTCATCTAACATAGGTATACCTAAG    1155

D  V  L  L  M  C  S  S  H  E  G  G  P  A  N  I  P  E  A  L  A  T  G  T  P  I  F  S  S  N  I  G  I  P  K
GATGTTGTTATTATAAGAATGGGTTGATTCTAACCTTAGATCCAGATATAGATGCTGAACAGATTAATTTTATTTGCCTTGAAAAACCAAATATATTTGAA    1260

D  V  V  I  N  Y  K  N  G  L  I  L  T  L  D  P  D  I  D  A  E  Q  I  N  F  I  C  L  E  K  P  N  I  F  E
AATATATTAGATTTTTCACTAAAACAGTCTCCAAGTTTAGCAATTTCTTGGGAGAAATGTATTCAACAAAATATTTTAGTTTATAAAAAAATAATTAAGGGTTAA    1365

N  I  L  D  F  S  L  K  Q  S  P  S  L  A  I  S  W  E  K  C  I  Q  Q  N  I  L  V  Y  K  K  I  I  K  G
TTATGTCCATTTCTATTCTAGTACCTGATTCTTTACACATTAACAAAAGAAACTTTAGTTCATTCTTCAGTTGGATTGAGAAAAATAAAATAAATATCCATTTTG    1470
CpsB →
   M  S  I  S  I  L  V  P  D  S  L  H  I  N  K  R  N  F  S  S  F  F  S  W  I  E  K  N  K  I  N  I  H  F
AAAATAATAATAAAGATTGGATTTCATTATATGGTTTTTACGATTCAAAATTGGGTATTCTATATGAGAAAATAGATATTCTTACTAAGATTGAAGAAGAGGAAT    1575

```
TATTTGCTTTTTGTGTTTATGATCTAAATATTTTCAATATTTGTAGAGCTGAATTATTATCTTTAGTAGCCACAAGACCCGAATGGTATAATGAAGATTATCCTA  1680

L F A F C V Y D L N I F N I C R A E L L S L V A T R P E W Y N E D Y P
ATAACTTAAGAGAAATATACAAAAAACTCTATACTAATAATCGAAGTGAATTATTGCAAAACATGGCTGCTGCTTGGTATTGGGTTGATTTCTGGAAAAAACGCC  1785

N N L R E I Y K K L Y T N N R S E L L Q N M A A A W Y W V D F W K K R
TATCTGAGTTAAAACAATTCTCTCATTGTTGTGTATTTTCAGGAGGTTTAATTTATCAAAAATCTTTGATTGAGTTATTAAAATATACTCCAACTAAAGTTATGG  1890

L S E L K Q F S H C C V F S G G L I Y Q K S L I E L L K Y T P T K V M
TTATGGAAAGCCTATTTACAGGAAACGAATATTATTGTGAGGAACGTTATTCATCAATTGCTAATAATAGCGATATTAAACATTTAGCTATTTTTAACTCTTATA  1995

V M E S L F T G N E Y Y C E E R Y S S I A N N S D I K H L A I F N S Y
AAAAAACATTTAGTTCAAAAAGTGAATATGATAAGGAACGAATGAAAGCTATTAATAAGTTCCTATTAATGAAAAATAAGAATGTCCAACAACCTACTGATTCTG  2100

K K T F S S K S E Y D K E R M K A I N K F L L M K N K N V Q Q P T D S
AAATATTAGTATTTAAACAACAAAAACCAATAATTACTATTATTGGACAAGTGATAAATGATTTTTCAGTCCTAGAATATAAAGGGAGAGGACTATCAACAATTA  2205

E I L V F K Q Q K P I I T I I G Q V I N D F S V L E Y K G R G L S T I
AAATCTATAAAGAACTTATATCTAAACTATCAGAGAATGGATTTAATGTAGTATTAAAAACTCACCCTTGGGAAGAGAAAAAAAATAATATCCGTACATCTTTAA  2310

K I Y K E L I S K L S E N G F N V V L K T H P W E E K K N N I R T S L
CTAAAAATATAATAGAAGAATTTCTAAAAAATCTAACTGAGAATCAACAAGAATGTATAAAAATAGTTGATCACTATTCAATAAAGAAATTATTTAAACAATCTG  2415

T K N I I E E F L K N L T E N Q Q E C I K I V D H Y S I K K L F K Q S
ATTTTATTATTAGTTTAAATTCTCAAGGGCTCCTTGAAGCTGCATTTGATGGTATAAAACCTATACAGTTAGGTAATGCTTTTTATGGAAAAAAAGGATTCACGT  2520

D F I I S L N S Q G L L E A A F D G I K P I Q L G N A F Y G K K G F T
ACGATTATGACTTTTTAGATATTGATCAATTGGTAAATGACTTAGTAGTAAATAAACTTACTCCAACACTATCTTTAGAAGAGTTTGATTTGTTCGAAGAGTTCA  2625

Y D Y D F L D I D Q L V N D L V V N K L T P T L S L E E F D L F E E F
TTACTATATTATTACAAAAGCATGCTGTTTCTATTCACGCCTCTGGCGTAAGTGTTTTATCTAGAATATTTAATTTACCTACTATTATACCATTAGTAGAAAATG  2730

I T I L L Q K H A V S I H A S G V S V L S R I F N L P T I I P L V E N
TCCCTAAGGAGAAGTCTAAAACAACATTACCTACTCAAAAAGATGTGGTAAAAAAGGAAAATACAACAATTGTTAATATGGTTGAGTTACCTAAAGTAGTTCCAC  2835

V P K E K S K T T L P T Q K D V V K K E N T T I V N M V E L P K V V P
AAAGTGATAAGAATAGGAAATATCAAAAATTTAGAAACAATCCTCGACAATTCTTTGCAGATTCTAGGAATCCAGTTATTAGAAGTTTAATGTATTTTTTCCCTT  2940

Q S D K N R K Y Q K F R N N P R Q F F A D S R N P V I R S L M Y F F P
ATAAATAATAGGTCTAATTTATGTTAAAAAAAATATCAGCCTTTTGATTTAAGAAAAATAAATGAAGGCCACTCTAGTAATGCTAAGTTAGTTTTACATTCTGA  3045

Y K . CpsC →  M L K K Y Q P F D L R K I N E G H S S N A K L V L H S E
GGCCTGTAATATAGATGCTAAAATCTCTAAGTTTTTCTGTTCACAAGATGACATTAATTTAGAAAACTTTATTGCAACATTTACTGATAACTATAAAGCACCAGA  3150

A C N I D A K I S K F F C S Q D D I N L E N F I A T F T D N Y K A P E
AGTATATACGGCGATTTTAAAGAATTGTTGTATTACACCTAGAGCACCTAAGCTACCAAGAT   3212
  V Y T A I L K N C C I T P R A P K L P R
```

```
CTAGACATTACATGATTAATTATAGGACGAGTCATTATGCTAGACATTAAAAATACTCCTGAAATACGAATACGTTATGGAGTTACCCTA   90

GATAGTTGATAAATTTTTCATCGGAATTTCATAAATATAAATGAGAAATTTATCAACTATCTAGGGGAAACTCCGTATTTTATATGGCTT  180

TTAAATTATAATGTTTATCTGTATAACGCCCCTCTTGATTTACTTTTTTTAAAAAAAATACATTTTTTAATTTGTTTGTAAATTTCTTA   270
         -35                 -10
TATTTAATTTCTCTTGATTAGGTAACTTATTAAAATCAATCTTTATGTGGATTTTAAGACATACCTATATAGTTGTTATTCCTTAATATA  360

TTGAAGAGAAATTAGATGAAACTCATCAAACTTAGATTACTCCTTTCTTTGGGGCTGGTTGCTAGTTTGGCTGCCTGCTCAAGCTTACCC  450
         CpxD →  M  K  L  I  K  L  R  L  L  L  S  L  G  L  V  A  S  L  A  A∇C  S  S  L  P
ACTTCAGGCCCTAGCCATAGTGCGATTTTAGAGGCTAATTCCCAGAACTCAGATAAACCTTTACCGGAAGTTAATTTAGTGGAGTTAGAT  540
  T  S  G  P  S  H  S  A  I  L  E  A  N  S  Q  N  S  D  K  P  L  P  E  V  N  L  V  E  L  D
AATGGCTTAGTTCAGCAGTTGTATCAGACTCAGCAAAGTCAGCAATTTTCCGGCTTTTTAGGCACGGCTGGCGGTGCTGGATATGCCGGT  630
  N  G  L  V  Q  Q  L  Y  Q  T  Q  Q  S  Q  Q  F  S  G  F  L  G  T  A  G  G  A  G  Y  A  G
GCGGTCAATGTGGGGGATGTTCTTGAAATTTCAATTTGGGAAGCGCCACCGGCAGTGTTGTTTGGCGGTACTTTTAGTTCTGAAGGGCAA  720
  A  V  N  V  G  D  V  L  E  I  S  I  W  E  A  P  P  A  V  L  F  G  G  T  F  S  S  E  G  Q
GGTAGCGGGCATTTAACGCAATTACCGGCGCAAATGGTTAACCAAAACGGTACGGTTACTGTGCCGTTTGTGGGTAATATTCGTGTTGCA  810
  G  S  G  H  L  T  Q  L  P  A  Q  M  V  N  Q  N  G  T  V  T  V  P  F  V  G  N  I  R  V  A
GGTAAAACACCGGAAGCGATTCAGTCTCAAATTGTTGGGGCATTGCAACGTAAAGCGAATCAGCCACAAGTATTAGTAAAAATTGCGAAT  900
  G  K  T  P  E  A  I  Q  S  Q  I  V  G  A  L  Q  R  K  A  N  Q  P  Q  V  L  V  K  I  A  N
AATAACTCTGCGGATGTTACGGTTATTCGTCAGGGTAACAGTATTCGTATGCCGCTGAGTGCGAATAACGAACGTGTGTTAGATGCTGTT  990
  N  N  S  A  D  V  T  V  I  R  Q  G  N  S  I  R  M  P  L  S  A  N  N  E  R  V  L  D  A  V
GCAGCAGTAGGCGGTACAACTGAAAATATTGAAGACGTTACCGTAAAATTAACTCGTGGCTCGCAAGTCAAAACATTAGCGTTTGAAACT 1080
  A  A  V  G  T  T  E  N  I  E  D  V  T  V  K  L  T  R  G  S  Q  V  K  T  L  A  F  E  T
CTAAATTTCCGATCCGGCGCAAAATATTATGTACGTGCCGGCGATGTCGTTTCGTTGCTAAACACGCCTTATAGCTTTACCGGTTTAGGT 1170
  L  I  S  D  P  A  Q  N  I  M  L  R  A  G  D  V  V  S  L  L  N  T  P  Y  S  F  T  G  L  G
GCGGTGGGTAACAACCAGCAAATGAAATTCTCAAGTAAAGGAATTACGCTTGCCGAAGCTATCGGTAAGATGGGTGGCCTAATTGATACT 1260
  A  V  G  N  N  Q  Q  M  K  F  S  S  K  G  I  T  L  A  E  A  I  G  K  M  G  G  L  I  D  T
CGTTCGGATCCGAGAGGGGTATTCGTCTTCCGTCATGTGCCTTTTTCTCAATTAAGTTTAGATCAGCAAACACAATGGGAGCGAAAGGC  1350
  R  S  D  P  R  G  V  F  V  F  R  H  V  P  F  S  Q  L  S  L  D  Q  Q  T  Q  W  G  A  K  G
TATGGTATGGGTATGGATGTACCGACGGTTTATCGTGTGAATTTACTTGAGCCGCAATCACTGTTTTTATTACAACGCTTCCCGATGCAA 1440
  Y  G  M  G  M  D  V  P  T  V  Y  R  V  N  L  L  E  P  Q  S  L  F  L  L  Q  R  F  P  M  Q
GATAAAGATATTGTCTATGTATCAAATGCACCGTTGTCCGAATTCCAAAAATTCTTGAGAATGATTTTCTCGATTACTTCGCCGGTTACA 1530
  D  K  D  I  V  Y  V  S  N  A  P  L  S  E  F  Q  K  F  L  R  M  I  F  S  I  T  S  P  V  T
```

FIG.10A

```
AGTACGACTAATGCTATTCGTGCCTATTAATATATTGAATTTATAAGGATAAAATATGGAAACAACTATTACGGCAAGTCCGACAGAAAA
 S  T  T  N  A  I  R  A  Y  .              CpxC →  M  E  T  T  I  T  A  S  P  T  E  K
                                                                                              1620
ACTACAAAAACCGGTTAAACAGAAAAAAAGTTGGTTAAAAAAGCTTAATCCGTTATTTTGGGTAACTGTAGCGATTCCTACGGTATTATC
 L  Q  K  P  V  K  Q  K  K  S  W  L  K  K  L  N  P  L  F  W  V  T  V  A  I  P  T  V  L  S
                                                                                              1710
AGCCTTTTATTTCGGTTCTGTTGCTTCCGATATTTATATTTCGGAATCAAGCTTCGTTGTAAGATCTCCTCAAAATCAGACCGCTTTAAC
 A  F  Y  F  G  S  V  A  S  D  I  Y  I  S  E  S  S  F  V  V  R  S  P  Q  N  Q  T  A  L  T
                                                                                              1800
CGGTGTCGGTGCCTTATTACAAGGTTCCGGATTTTCTCGAGCTCAAGATGATACTTATACCGTACAAGAATATATGCATTCTCGTACGGC
 G  V  G  A  L  L  Q  G  S  G  F  S  R  A  Q  D  D  T  Y  T  V  Q  E  Y  M  H  S  R  T  A
                                                                                              1890
ACTAGAACAGTTAATGAAAGACTTGCCAATACGTGAATACTATGAGAATCAAGGCGATATTATCGCTCGCTTTAATGGATTTGGTTTAAA
 L  E  Q  L  M  K  D  L  P  I  R  E  Y  Y  E  N  Q  G  D  I  I  A  R  F  N  G  F  G  L  N
                                                                                              1980
TAATAGTAAAGAAGCGTTTTATAAATATTTCCGAGATCGCTTAAGTGTGGACTTTGACTCTGTTTCCGGTATCGCCAGCTTACGTATTCG
 N  S  K  E  A  F  Y  K  Y  F  R  D  R  L  S  V  D  F  D  S  V  S  G  I  A  S  L  R  I  R
                                                                                              2070
AGCATTTAACGCGGAAGAGGGGCAACAAATTAATCAAAAATTACTTGCCGAAGGTGAAACGCTTATTAACCGTTTAAACGAACGTGCAAG
 A  F  N  A  E  E  G  Q  Q  I  N  Q  K  L  L  A  E  G  E  T  L  I  N  R  L  N  E  R  A  R
                                                                                              2160
AAAAGATACCATTTCATTTGCCGAACAAGCGGTTACAGAAGCGGAAAATAATGTAAACGAAACGGAAATGCTTTAAGTAAATACCGTAT
 K  D  T  I  S  F  A  E  Q  A  V  T  E  A  E  N  N  V  N  E  T  A  N  A  L  S  K  Y  R  I
                                                                                              2250
CAAAAATAAAATCTTTGATTTACCGGCACAATCCGGCGTACAACTTTCATTAATTTCCAGCCTAAAAAGCGAATTGATTCGTGTAGAAAC
 K  N  K  I  F  D  L  P  A  Q  S  G  V  Q  L  S  L  I  S  S  L  K  S  E  L  I  R  V  E  T
                                                                                              2340
ACAATTGGCTCAATTGCAATCTATTACACCGGACAACCCACAAGTTGATGCATTGCTTATGCGCCAAAAAAGTTTACGTAAGGAAATCGA
 Q  L  A  Q  L  Q  S  I  T  P  D  N  P  Q  V  D  A  L  L  M  R  Q  K  S  L  R  K  E  I  D
                                                                                              2430
TGAGCAATCAAAACAGCTTTCCAGTAACAGTAATAGCTCTATTGCTATTCAAACTGCCGATTACCACCGCTTAGTACTTGCAAACGAGCT
 E  Q  S  K  Q  L  S  S  N  S  N  S  S  I  A  I  Q  T  A  D  Y  Q  R  L  V  L  A  N  E  L
                                                                                              2520
GGCACAGCAACAATTGACCGCAGCATTAACCTCATTACAAAATACGAAAAATGAAGCGGATCGCCAGCAACTTTATTTAGAAGTAATCAG
 A  Q  Q  Q  L  T  A  A  L  T  S  L  Q  N  T  K  N  E  A  D  R  Q  Q  L  Y  L  E  V  I
                                                                                              2610
TCAGCCAAGCAAACCGGACTGGGCGGAAGAGCCTTATCGCTTATATAATATTTTAGCGACATTCTTTATCGGTCTGATGCTTTATGGTGT
 Q  P  S  K  P  D  W  A  E  E  P  Y  R  L  Y  N  I  L  A  T  F  F  I  G  L  M  L  Y  G  V
                                                                                              2700
ATTAAGTTTATTAATTGCAAGCGTAAGAGAGCACAAAAACTAATGCAATACGGTGATCAAACAACTTTCCGCCAATCTCTCGCCATTCAA
 L  S  L  L  I  A  S  V  R  E  H  K  N  .         CpxB →  M  Q  Y  G  D  Q  T  T  F  R  Q  S  L  A  I  Q
                                                                                              2790
GGGAGAGTAATCGGTGCATTACTCATGCGGGAAATTATTACGCGTTACGGACGAAAAAATTTGGGTTTTTTATGGCTGTTTGTTGAGCCG
 G  R  V  I  G  A  L  L  M  R  E  I  I  T  R  Y  G  R  K  N  L  G  F  L  W  L  F  V  E  P
                                                                                              2880
CTATTACTCACTTTATTTATCGTTTTGATGTGGAAATTTATCCGAGCGGATCGCGTTTCCGATTTAAATATTATTGCTTTTGTGATTACC
 L  L  L  T  L  F  I  V  L  M  W  K  F  I  R  A  D  R  V  S  D  L  N  I  A  F  V  I  T
                                                                                              2970
GGTTATCCAATGGCCATGATGTGGCGTAATGCGTCAAACCGCACTATCGGTGCAATTTCCGGTAACTTGAGTCTTCTTTATCATCGTAAT
 G  Y  P  M  A  M  M  W  R  N  A  S  N  R  T  I  G  A  I  S  G  N  L  S  L  L  Y  H  R  N
                                                                                              3060
GTTCGCGTATTAGATACCTTACTGGCTCGTGTCATACTTGAAGTAGCAGGTGCAACGATTGCCCAAATCATTATTATGGCATTAGTCATT
 V  R  V  L  D  T  L  L  A  R  V  I  L  E  V  A  G  A  T  I  A  Q  I  I  I  M  A  L  V  I
                                                                                              3150
```

FIG.10B

RECOMBINANT VACCINE FOR DISEASES CAUSED BY ENCAPSULATED ORGANISMS

RELATED APPLICATION

This application is a continuation of U.S. patent application Ser. No: 08/673,814, filed of Jun. 27, 1996, the complete comtents of that application is herein incorporated by reference.

BACKGROUND OF THE INVENTION

1. Field of the Invention

The invention relates generally to vaccines used in veterinary applications and, more particularly, to a live, recombinant, attenuated vaccine for disease states that are caused by organisms that include capsule where the presence of the capsule is required for virulence but not immunoprotection. The invention has specific application to a recombinantly produced vaccine that has been engineered such that it lacks capsule.

2. Description of the Prior Art

Vaccines are preparations used to prevent specific diseases in animals and humans by inducing immunity. This is accomplished by exposing a patient to an antigen for a particular disease which, in turn, causes the immune system of the patient to produce large quantities of antibody. The presence of the antibody in the patient's blood protects the patient from a later attack by the disease causing agent. Vaccines may either be composed of subunits of the agent, or the live or killed agent itself For example, poliomyelitis, commonly referred to as "polio", is typically prevented by either administering a live, attenuated oral poliovirus vaccine, which is common practice for treating children, or by administering a killed or inactivated poliovirus vaccine, which is the usual practice for treating adults since they are generally at higher risk for contracting polio from the live vaccine. If a live vaccine is to be used, its virulence must be attenuated in some way; otherwise the virus in the vaccine will cause the disease it is intended to protect against.

A number of diseases are caused by encapsulated bacteria wherein the capsule, which is the gum-like layer of polysaccharide or polypeptide exterior to the cell wall of these bacteria, is required for pathogenesis. Swine pleuropneumonia is one example, and virulence factors for *Actinobacillus pleuropneumoniae*, the bacterium which causes the disease, include capsular polysaccharide, endotoxin, and protein exotoxins. Swine pleuropneumonia is one of the major respiratory diseases affecting swine production throughout the world, and accounts for millions of dollars in annual losses to the industry in the United States alone.

U.S. Pat. No. 5,429,818 to Inzana, which is herein incorporated by reference, discloses that non-encapsulated mutants of *Actinobacillus pleuropneumoniae* are a virulent and capable of providing excellent protection against subsequent exposure to the virulent bacteria. The non-capsulated mutants described in Inzana were prepared by ethylmethanesulfunate mutagenesis. However, such procedures have the disadvantages that some spontaneous or chemically induced mutants may not be stable, and the nature of the mutation(s) is (are) unknown.

SUMMARY OF THE INVENTION

It is an object of this invention to provide a safe and effective, live, attenuated, recombinant vaccine for diseases caused by bacteria and fungi which are normally encapsulated and where the capsule is required for virulence but not immunoprotection.

It is another object of this invention to genetically engineer certain bacteria or fungi to lack capsule such that they are rendered a virulent and the genetic nature of the mutation is known.

It is yet another object of this invention to provide a safe and effective, live, attenuated, recombinant vaccine for pleuropneumonia.

According to the invention, a recombinant, live, attenuated strain of *Actinobacillus pleuropneumoniae* which has been genetically engineered to lack capsule has been produced. Since the capsule is required for virulence, but not immunoprotection, the strain will be useful as a vaccine against swine pleuropneumonia. The vaccine was produced by cloned plasmid vector that cannot replicate in *A. pleuropneumoniae*. The capsule export and synthesis genes of *A. pleuropneumoniae* serotype 5 were sequenced. A large deletion was made in the cloned synthesis genes for the capsule, and genes encoding for kanamycin resistance and sucrose sensitivity were then cloned into the deleted site to serve as marker genes. This suicide vector was inserted into a virulent *A. pleuropneumoniae* serotype 5 strain using electroporation in order to obtain a homologous recombination event by double cross over between homologous regions of the chromosome and plasmid. Four isolates were obtained, and each lacked iridescence suggesting a lack of capsule. The lack of capsule and the deleted region of the capsule genes was confirmed in one strain by dot blotting and Southern blotting, respectively. The presence of the marker genes in the recombinant strain was also confirmed. No other change in any other phenotypic properties could be identified, and the marker genes were not found in other regions of the chromosome. The recombinant strain, referred to as J45-100, was very serum sensitive, had reduced virulence in pigs at ten times the 50% lethal dose for the parent strain, and should provide protection for swine against pleuropneumonia.

This invention will be useful for producing vaccines against any encapsulated organism that produces toxins or other virulence factors where the capsule is required for virulence but not immunoprotection. All that will be required will be to clone the genes encoding for capsule synthesis for the organism, and then delete and replace the section of the cloned gene with a marker gene on a suicide vector, and then introduce the vector into the desired organism and screen for a genetically modified organism that lacks capsule. The invention should be useful in producing vaccines for additional bacteria infectants including, but not limited to, *Pasteurella multocida, Pasteurella haemolytica,* and *Pseudomonas aeruginosa*, as well as fungi such as *Cryptococcus neofornans* which is a pathogen associated with acquired immune deficiency syndrome (AIDS) in cats and humans.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a physical map of pCW-11E cloned DNA from the capsule synthesis region of *A. pleuropneumoniae* J45. The location and direction of transcription of the two complete ORFs (cpsA and cpsB, solid fill) identified by dideoxy sequencing is indicated. The location of a partial third potential ORF (cpsC) is also indicated. The location and direction of transcription of the incomplete capsule export gene cpxD located on this DNA fragment is also indicated. The 2.1 kb Bglll-StuI fragment used as the DNA probe in FIG. 2 is indicated. Dotted fill indicates incomplete ORFs.

FIG. 2 is a southern blot analysis of *A. pleuropneumoniae* genomic DNA hybridized to the digoxigenin-labeled 2.1 kb Bglll-StuI fragment of pCW11E. BamHI-digested genomic DNA from serotype 1 strain 4074 (lane 1), serotype 2 strain 1536 (lane 2), serotype 5a strain J45 (lane 3), serotype 5a strain K17 (lane 4), serotype 5 strain 178 (lane 5), serotype 7 strain 29628 (lane 6), and serotype 9 strain 13261 (lane 7) were hybridized with the probe as described below. The molecular mass of the hybridizing bands (in kb) is indicated.

FIGS. 3a and 3b present the nucleotide sequence of the 3.2 kb Hindlll-EcoRV fragment of pCW-11E, containing the serotype-specific *A. pleuropneumoniae* J45 DNA (SEQ ID NO. 1). The deduced amino acid sequences of the two complete ORFs detected in this sequence, cpsA (SEQ ID NO.2) and cpsB (SEQ ID NO.3), and the deduced N-terminal sequence of a third incomplete ORF, cpsC (SEQ ID NO. 4), are indicated below the nucleotide sequence. Putative ribosome-binding sites preceding each ORF are in boldface, and putative −10 and −35 promoter sequences upstream from cpsA are indicated.

FIG. 9 shows the bactericidal activity of precolostral calf serum for *A. pleuropneumoniae* J45 and J45-100. Percent viability of bacterial strains was evaluated after 60 minutes incubation at 37° C. Each data point represents the mean of three separate experiments performed in duplicate. Error bars represent the standard deviation for each mean. The maximum percent viability recorded for J45 was 100%, although these values were typically higher because the bacteria usually grew during the experiment. Values greater than 100% were not recorded because they could not be accurately determined.

FIGS. 10a and 10b present the nucleotide sequence of the 3.2 kb XbaI-ClaI fragment of pCW-1C encoding for the capsule export genes of *A. pleuropneumoniae* J45 DNA (SEQ ID NO.5). The deduced amino acid sequences (SEQ ID Nos.6–9) of proteins involved in the export of the *A. pleuropneumoniae* serotype 5a capsular polysacharide are presented.

DETAILED DESCRIPTION OF THE PREFERRED EMBODIMENTS OF THE INVENTION

The invention contemplates using a live, recombinantly produced, a virulent, strain of a microorganism (i.e., bacteria or fungus) which has been genetically engineered to be non-capsulated as a vaccine against diseases caused by the microorganism. The invention will have utility in preventing diseases wherein the capsule of the microorganism is required for virulence but not immunoprotection, and where the disease is caused by toxins or other virulence factors. As a particular example of the invention, a non-capsulated strain of *Actinobacillus pleuropneumoniae* has been produced and should be useful as a vaccine against pleuropneumonia in swine. The chief feature of the invention is the genetic modification of the microorganism, which, in a specific embodiment is *Actinobacillus pleuropneumoniae*, to include a deletion in its deoxyribonucleic acid (DNA) in the region encoding for capsule synthesis. For exemplary purposes only, the synthesis of a transformed *Actinobacillus pleuropneumoniae* serotype 5 mutant is disclosed; however, it should be understood that other serotypes could be prepared in a manner similar to that which is described below, and would be useful in a vaccine alone or in combination with one or more recombinant mutants of different serotypes.

The strain described below, along with other strains of noncapsulated, toxigenic bacteria or other microorganisms generated according to the procedures described below, will make excellent vaccines because they are a virulent, but produce all the antigens necessary for the host to make a protective immune response. The vaccines can be administered by a variety of methods; however, intramuscular or subcutaneous injection is preferred. The advantage of these live vaccines is that the toxins that are primarily responsible for the disease and other components only made by live organisms or in vivo, will be made at the immunization site and the host will make an immune response which protects itself from the lesions caused by the toxins. Hence, the disease (acute or chronic) does not occur. The organisms cannot disseminate, however, because without capsule, they are extremely serum sensitive, and are cleared immediately in the bloodstream or respiratory tract. In addition, as a live vaccine, the cell-mediated immune response will be greater and the protection will last longer than with killed vaccines.

EXAMPLE

A DNA region involved in *Actinobacillus pleuropneumoniae* capsular polysaccharide biosynthesis was identified and characterized. A probe specific for the cpxD gene involved in the export of the *A. pleuropneumoniae* serotype 5a J45 capsular polysaccharide was used to identify and clone an adjacent 5.8 kilobase BamHI fragment of J45 genomic DNA Southern blot analyses demonstrated that a portion of this region contained DNA that was serotype-specific. DNA sequence analysis demonstrated that this region contained two complete open reading frames, cpsA and cpsB, and an incomplete potential third open reading frame, cpsC. cpsA and cpsB shared some low homology with glycosyltransferases involved in the biosynthesis of *Escherichia coli* lipopolysaccharide and *Haemophilus influenzae* type b capsular polysaccharide, respectively. A 2.1 kilobase deletion which spanned the cloned cpsABC open reading frames was constructed and recombined into the J45 chromosome by allelic exchange to produce the mutant J45-100. This mutant did not produce intracellular or extracellular capsular polysaccharide, indicating that cpsA, cpsB, and/or cpsC were involved in *A. pleuropneumoniae* capsular polysaccharide biosynthesis. The Apx toxin and lipopolysaccharide profiles of J45-100 were identical to the encapsulated parent strain, J45. However, J45-100 grew faster in vitro than J45. J45-100 was sensitive to killing in precolostral calf serum, whereas J45 was not. J45-100 was a virulent when used to challenge pigs intratracheally with 3 times the 50% lethal dose of strain J45. At 6 times the 50% lethal dose of J45, J45-100 caused mild to moderate lung lesions, but not death. These results demonstrated that the capsular polysaccharide is a major determinant of serum-resistance and virulence of *A. pleuropneumoniae*.

MATERIALS AND METHODS

Bacterial Strains, Plasmids, and Growth Conditions

The bacterial strains and plasmids used in this study are as described in Table 1. For genomic DNA extraction and for bactericidal assays, *A. pleuropneumoniae* strains were grown with shaking at 37° C. in brain heart infusion broth (Difco Laboratories, Detroit, Mich.) containing 5 µg/ml nicotinamide adenine dinucleotide (NAD) (Sigma Chemical Co., St. Louis, Mo.). For electroporation, *A. pleuropneumoniae* strains were grown with shaking at 37° C. in tryptic soy broth (Difco Laboratories) containing 0.6% yeast extract (Difco Laboratories) and 5 µg/ml NAD (TSY-N). For pig challenge experiments, *A. pleuropneumoniae* strains were grown with shaking at 37° C. in Columbia broth (Difco Laboratories) containing 5 µg/ml NAD. *Escherichia coli* strains were grown in Luria-Bertani broth (Sambrook et al., 1989) for routine cultivation, or in Terrific broth (Tartof and Hobbes, 1987) for extraction of plasmids. Antibiotics were used in growth media for maintenance of plasmids in *E. coli* at the following concentrations: ampicillin (Amp) 100 µg/ml, and kanamycin (Kan) 50 µg/ml. Kanamycin was used at 85 µg/ml for selection of *A. pleuropneumoniae* recombinant mutants.

TABLE 1

Bacterial strains and plasmids used.

| Strain or plasmid | Relevant genotype or characteristics | Source or reference |
|---|---|---|
| *A. pleuropneumoniae* Strains | | |
| 4074 | serotype 1; (ATCC 27088) | ATCC[a] |
| 1536 | serotype 2; (ATCC 27089) | ATCC[a] |
| J45 | serotype 5a | Fenwick et al., 1986a |
| K17 | serotype 5a | Nielsen, 1986a |
| 178 | serotype 5 | M. Mulks |
| 29628 | serotype 7 | L. Hoffman |
| 13261 | serotype 9 | J. Nicolet |
| J45-C | noncapsulated mutant isolated after ethyl methanesulfonate mutagenesis of strain J45 | Inzana et al., 1993a |
| J45-100 | recombinant noncapsulated mutant derived from strain J45 | This chapter |
| *E. coli* Strains | | |
| XL1-Blue | recA1 endA1 gyrA96 thi-1 hsdR17 supE44 relA1 lac(F⁺ proAB lac<sup>q</sup>ZΔM15 Tn10); Host for recombinant plasmids | Stratagene, La Jolla, Calif. |
| Plasmids | | |
| pGEM-3Z | Cloning vector, 2.74 kb; Amp<sup>r</sup> | Promega |
| pCW-1C | 5.3 kb XbaI fragment of J45 cloned into pGEM-3Z | Chapter 3 |
| pCW-11E | 5.8 kb BamHI fragment of J45 cloned into pGEM-3Z | This work |

TABLE 1-continued

Bacterial strains and plasmids used.

| Strain or plasmid | Relevant genotype or characteristics | Source or reference |
|---|---|---|
| pKS | 3.8 kb BamHI fragment containing the nptl[b]-sacRB cartridge[c] cloned into the BamHI site of pGEM-3Z; Amp[r], Kan[r] | S. M. Boyle |
| pCW11EΔ1KS1 | pCW-11E with the 2.1 kb BglII -StuI fragment deleted and the 3.8. kbBamHI nptl-sacRB cartridge from pKS ligated in | This chapter |

[a]American Type Culture Collection, Rockville, Md.
[b]This marker was originally derived from the Tn903 nptl gene of pUC4K (Pharmacia Biotech, Piscataway, N.J.).
[c]This cartridge has been previously described (Ried and Collmer, 1987).

Calculation of Generation Time

The generation time of logarithmic phase *A. pleuropneumoniae* strains grown in TSY-N was calculated using the equation: R=1/g, where R is the average rate of bacterial growth, and g is the generation time of the bacterial population (Pelczar et al., 1993). The average rate of growth, R, was calculated using the following equation: R=3.32 ($\log_{10}N-\log_{10}N_0$)/t, where t is the elapsed time, N is the number of bacteria at time=t, and $N_0$ is the initial number of bacteria at time=0 (Pelczar et al., 1993).

DNA Hybridization Analysis

Restriction endonuclease-digested DNA (approximately 5 μg per lane) was electrophoresed through 0.7% agarose gels and was transferred by capillary action to MagnaGraph nylon membranes (Micron Separations Inc., Westboro, Mass.) using 20× saline sodium citrate (20×SSC is 3 M NaCl, 300 mM sodium citrate, pH 7) as previously described (Sambrook et al., 1989; Southern, 1975). DNA was covalently linked to nylon membranes by ultraviolet irradiation using a UV Stratalinker (Stratagene, La Jolla, Calif.). Digoxigenin-labeled probes for DNA hybridizations were synthesized by the random primer method using the Genius System nonradioactive labeling and detection kit (Boehringer-Mannheim Corp., Indianapolis, Ind.) according to the manufacturer's directions. DNA hybridizations were performed at 68° C. in solutions containing 5×SSC. The membranes were washed and developed according to the Genius System directions for calorimetric detection.

Recombinant DNA Methods and Reagents

Genomic DNA was isolated from broth-grown *A. pleuropneumoniae* cells using a method described by S. Spinola. Briefly, bacteria were resuspended in 10 mM Tris-1 mM EDTA (pH 8) and incubated with sodium dodecyl sulfate (0.66%), and RNAse (100 μg/ml) for 1 hour at 37° C. Proteinase K was added to a final concentration of 100 μg/ml, and the mixture was incubated at 56° C. for 1 hour. The mixture was extracted once with buffered phenol and four times with buffered phenol-chloroform (Amresco, Inc., Solon, Ohio), and the genomic DNA was ethanol precipitated and resuspended in 10 mM Tris-1 mM EDTA (pH 8). Plasmid DNA was isolated by a rapid alkaline lysis method (Ish-Horowicz and Burke, 1981). Restriction fragments required for cloning and probe synthesis were eluted from agarose gels as described (Zhen and Swank, 1993). Restriction digests, agarose gel electrophoresis, and DNA ligations were performed as previously described (Sambrook et al., 1989). Restriction fragment ends were made blunt-ended by filling in 5' overhangs with nucleotides (dNTPs) using the Klenow fragment of DNA polymerase 1, as previously described (Sambrook et al., 1989). Plasmid DNA was transformed into *E. coli* strains by electroporation (Dower et al., 1988) using a BTX ECM 600 electroporator (BTX Inc., San Diego, Calif.).

Restriction endonucleases and the Klenow fragment of DNA polymerase I were obtained from Promega Corporation (Madison, Wis.). T4 DNA ligase was obtained from Gibco BRL (Gaithersburg, Md.). Nucleotides (dNTPs) for fill-in reactions were obtained from Boehringer-Mannheim Corporation (Indianapolis, Ind.).

DNA Sequencing and Analysis

The nucleotide sequence of both strands of the 2.7 kilobase (kb) XbaI-EcoRV DNA fragment of pCW-11E was determined by the dideoxy chain-termination method (Sanger et al., 1977) using the Sequenase version 2.0 DNA sequencing kit (United States Biochemical Corp., Cleveland, Ohio) with $\alpha^{35}$[S]dATP (DuPont/NEN Research Products, Boston, Mass.). Double stranded DNA templates were sequenced using custom, oligonucleotide primers (DNAgency, Inc., Malveme, Pa.) to continue reading along each strand.

The nucleotide sequence obtained was combined with the nucleotide sequence of the 4.6 kb XbaI-ClaI DNA fragment of pCW-1C encoding for the upstream capsule structural genes (FIG. 10), and was analyzed using DNASTAR analysis software (DNASTAR, Inc, Madison, Wis.). Sequence similarity searches of the EMBUGenBank/DDBJ databases were performed using BLAST software (Altschul et al., 1990) at the National Center for Biotechnology Information (Bethesda, Md.).

Figure 11:
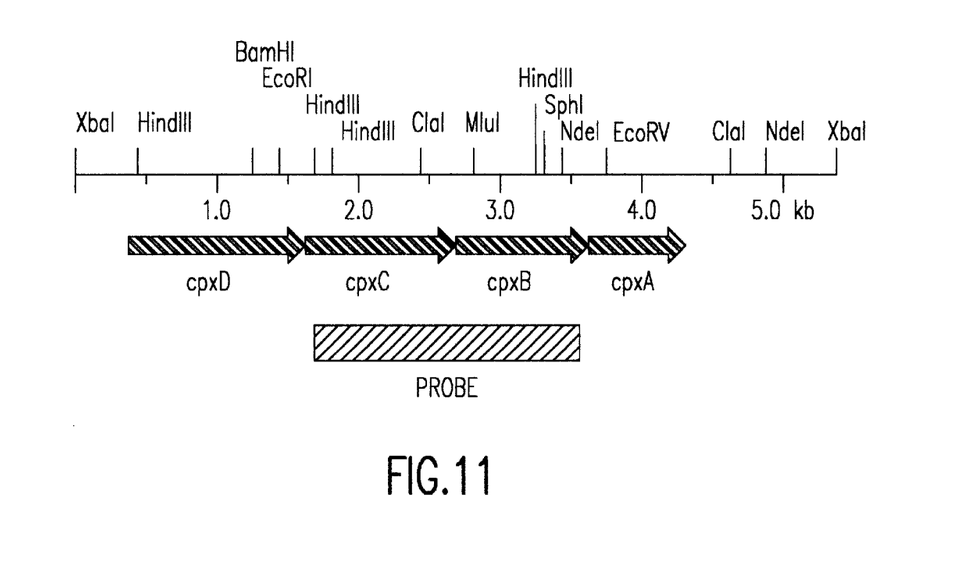
FIG. 11 is a physical map of pCW-1C DNA from *A. pleuropneumoniae* J45.

Conserved regions of the *H. influenza* type b cap (capb) locus involved in capsular polysaccharide export was used to identify, clone, and characterize a portion of the *A. pleuropneumoniae* serotype 5a capsulation locus involved in capsular polysaccharide export. Southern blot analyses of *A. pleuropneumoniae* serotype 5a strain J45 genomic DNA with probes specific for contiguous regions of the *H. influenzae* type b capsulation (capb) locus were performed. These probes did not hybridize to *A. pleuropneumoniae* genomic DNA under conditions of high stringency (68° C., 5×SSC), but did hybridize under conditions of medium-to-low stringency (55° C., 5×SSC). A 4.4 kb EcoRI fragment of the *H. inlfluenzae capb* locu from the plasmid pSKH1 containing the region 1 bexD gene involved in capsular polysaccharide export and two region 2 open reading frames (ORFs) involved in capsular polysaccharide biosynthesis, hybridized to 1.2 kb HindIII and 5.3 kb XbaI fragments of J45 genomic DNA. A 9.0 kb EcoRI fragment of the *H.influenzae* capb locus from the plasmid pSKH2, containing the region 1 bexCBA genes involved in capsular polysacharide export, some uncharacterized region 3 DNA common to several *H. influenzae* serotypes, and some region 2 DNA idvolved in capsular polysaccbaride biosynthesis, hybridized to 1.5 kb HindIII, 5.3 kb XbaI, and 2.4 kb XhoI fragments of J45 genomic DNA. These data indicated That tie *H. influenzae* type b and *A. pleuropneumoniae* serotype 5a capsule gene loci shared homologous regions. The *H. influenzae* cupb specific probes both contain region 1 DNA involved in capsular polysacchandc export, suggesting that the 5.3 XbaI genomic DNA fragment from J45 that hybridized to both *H. influenzae* capb probes may contain genes that encode proteins involved in export of the *A. pleuropneumoniae* serotype 5a capsular polysaccharide. The 5.3 XbaI genomic DNA fragment from J 45 that hybridized to the two *H. influenzae* capb probes was cloned into the XbaI site of the plasmid pGEM-3Z (in both orientations) from XbaI-digested J45 genomic DNA fragments in the range of 4.8 to 6.0 kb that were electroluted (following electrophoretic separation) from an agarose gel. One of the resulting plasmids was designated pCW-1C. A deposit of this plasmid (in the host bacterium *E. coli*) was made on May 15, 2001 at the American Type Culture Collection (ATTC), 10801 University Blvd., Manassas, Va, USA, under Accession No. PTA-3345. Southern blots were peformed to determine if the *H. influenzae* type b bexD, bexC, bexB, and bexA hybridized to adjacent fragments of pCW-1C in the same order (bexDCBA) in which the segenes occur in *H. in fluenzae*. The results suggested that the *A. pleuropneumaniae* serotype 5a DNA region required for capsular polysaccharide export had been successfully cloned, and that this region was organized in a similar manner to the *H. influenzae* type b bex locus The nucleotide sequence of the 4.6 kb XbaI-ClaI restriction fragment of pCW-1C was determined and a 3.2 kb XbaI-ClaI restriction fragment is presented in FIGS. 10*a–b* SEQ. ID NO.5. Four ORFs (shown in FIGS. 10*a–b* and FIG. 11) designated cpxDCBA (cpx is used to designate capsular polysacharide export) were detected in close proximity on the same DNA strand. The AUG initiation codon of cpxC (SEQ ID NO.7) was 26 nucleotides downstream from the UAA termination codon of cpxD (SEQ ID NO.6), whereas the AUG initiation codon of cpxB (SEQ ID NO.8) overlapped the UAA termination codon of cpxC (SEQ ID NO.7), and the AUG initiation codon of cpXA (not shown) overlapped the UGA termination codon of cpxB partialy shown (SEQ ID NO. 8). Shine-Dalgarno ribosome binding consensus sequences were identified within 17 bases upstream of each AUG initiation codon and a putative promoter containing sequences similar to *E. coli* $\sigma^{70}$–10 (TATAAT) and–35 (TTGACA) consensus sequences was identified upstream of cpxD (SEQ ID NO. 6). A palindromic sequence which may function as a rho-independent transcription termination signal was identified downstream of cpxA (SEQ ID NO. 9). The genetic organization suggests that cpxDCBA are transcribed onto a singel, polycistronic mRNA.

Electrotransformation of *A. pleuropneumoniae*

*A. pleuropneumoniae* was grown to midlogarithmic phase in TSY-N, pelleted by centrifigation at 7000×g at 4° C., and washed four times in a chilled (4° C.), filter-sterilized buffer containing 272 mM mannitol, 2.43 mM K2HP04, 0.57 mM KH2P04, 15% glycerol, pH 7.5. This buffer was modified (to contain mannitol in place of sucrose) from a previously described buffer used for washing *A. pleuropneumoniae* cells prior to electroporation (Lalonde et al., 1989b). The cells were then washed one time in chilled, filter-sterilized 15% glycerol, and resuspended to approximately $10^{10}$ CFU/ml in 15% glycerol. Aliquots of this suspension (90 µl) were mixed with 1.5–2.0 µg of plasmid DNA (in 1.5 µl distilled water) that had been purified by cesium chloride density gradient ultracentrifugation (Sambrook et al., 1989), placed in chilled 2 mm gap electroporation cuvettes (BTX, Inc.), and electroporated using a BTX ECM 600 electroporator (BTX, Inc.) set to a charging voltage of 2.5 kV and to a resistance setting of R7 (246 ohms). The actual pulse generated was 2.39 kV delivered over 10.7 milliseconds. After electroporation, the cells were recovered in 1 ml TSY-N containing 5 mM $MgCl_2$ with gentle shaking for 3.5 hours at 37° C. After recovery, the cells were cultured on TSY-N agar containing 85 µg of kanamycin per ml and were incubated at 37° C.

Immunoblotting

For colony immunoblots, *A. pleuropneumoniae* whole cells grown overnight on TSY-N agar plates were scraped into phosphatebuffered saline (PBS) and adjusted to $10^9$ CFU/ml, as determined spectrophotometrically. Approximately $5\times10^4$ or $5\times10^5$ CFU per well was applied to a nitrocellulose membrane (NitroBind; Micron Separations Inc.) using a Bio-Dot apparatus (Bio-Rad Laboratories, Richmond, Calif). The membrane was placed in chloroform for 15 minutes at room temperature to Iyse the bacterial cells on the membrane. The membrane was air dried completely, and incubated for 1 hour at room temperature in Tris-buffered saline, pH 7.5 (TBS) containing 2% skim milk to block nonspecific binding sites on the membrane. The membrane was incubated for 1 hour at room temperature in a 1:200 dilution (in 2% milk-TBS) of an adsorbed swine antiserum that contained antibodies to the serotype 5a capsular polysaccharide, but not other *A. pleuropneumoniae* surface antigens. This capsular polysaccharide-enriched antiserum was prepared by adsorbing hyperimmune swine antiserum to *A. pleuropneumoniae* K17 with a spontaneous noncapsulated mutant, K17-C (Inzana and Mathison, 1987), as described previously (Inzana, 1995). The membrane was washed in TBS containing 0.05% Tween 20, then incubated 1 hour at room temperature in a 1:1000 dilution of rabbit anti-swine IgG conjugated to horseradish peroxidase (heavy and light chains; Cappel, Durham, N.C.). The membrane was washed in TBS, then developed with 4-chloro-1-naphthol (Bio-Rad Laboratories) in TBS containing 0.02% $H_2O_2$.

Immunoblotting of *A. pleuropneumoniae* concentrated culture supernatants was performed as described previously (Ma and Inzana, 1990). Briefly, approximately 15 µg of total culture supernatant protein was separated by discontinuous SDS-PAGE (Laemmli, 1970) through an 8% separating gel. The proteins were transferred to a nitrocellulose membrane (NitroBind; Micron Separations Inc.) by the method of Towbin et al. (1979). The membrane was incubated in TBS containing 2% bovine serum albumin to block nonspecific binding and was cut into strips. The strips were incubated overnight at 4° C. with either a monoclonal antibody specific for the Apxll toxin (Ma and Inzana, 1990) or a monoclonal antibody specific for the Apxl toxin (Devendish et al., 1989; Frey et al., 1992), and washed in TBS. The blot reacting with the Apxll-specific monoclonal antibody was incubated with a 1:2000 dilution of goat anti-mouse IgG conjugated to horseradish peroxidase (Cappel), washed in TBS, and developed as described above. The blot reacting with the Apxl-specific monoclonal antibody was incubated with a 1:2000 dilution of goat anti-mouse IgG conjugated to alkaline phosphatase and developed as described previously (Frey et al., 1992).

LPS Extraction and Electrophoresis

LPS was isolated from *A. pleuropneumoniae* using a micro hot phenol-water extraction method, as previously described (Inzana, 1983). Purified LPS was electrophoresed through a 15% polyacrylamide separating gel containing urea, as described (Inzana et al., 1988). LPS electrophoretic profiles were visualized by staining the gel with ammoniacal silver (Tsai and Frasch, 1982).

Serum Bactericidal Assay

Sensitivity of A. pleuropneumoniae to the bactericidal activity of precolostral calf serum was determined. Percent viability of bacterial strains in 5, 10, 15, 20, 30, 40, and 50% precolostral calf serum was evaluated after 60 minutes incubation at 37° C.

Virulence Study

Pigs 7 to 9 weeks of age were obtained from two local herds free from A. pleuropneumoniae infection and were distributed randomly into groups. Groups of pigs were housed in separate pens with no direct physical contact permitted between each group. The animal facilities at Virginia Polytechnic Institute and State University are operated and maintained in accordance with the requirements of the American Association for Accreditation of Laboratory Animal Care. For the challenge experiment, A. pleuropneumoniae strains were grown with shaking in Columbia broth (Difco Laboratories) supplemented with 5 μg/ml NAD attion at 7000×g and resuspended to approximately $10^9$ CFU/ml in PBS. Pigs were challenged intratracheally with 10 ml of a dilution of this suspension following mild sedation with Stresnil (Pittman-Moore, Inc., Washington Crossing, N.J.). Pigs were necropsied as soon as possible after death or immediately after euthanasia with sodium pentobarbital. Lung lesions were scored by a veterinary pathologist according to the following criteria: 0, unremarkable lungs (no gross lesions observed); 1+, 1–10% of lung tissue affected by some combination of congestion, edema, hemorrhage, consolidation, and/or pleuritis; 2+, 11–49% of lung tissue affected; 3+, 50–74% of lung tissue affected; 4+, 75% or greater of lung tissue affected. Lung samples were taken at necropsy from the right cranial-dorsal aspect of the caudal lobe and cultured on brain heart infusion medium containing NAD to detect the presence of A. pleuropneumoniae.

RESULTS

Figure 1:
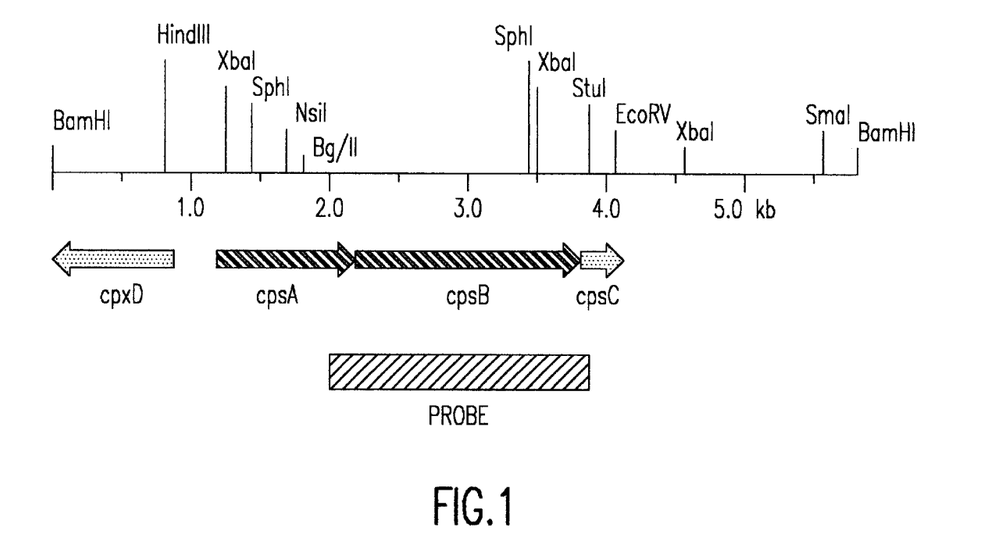

Identification and Cloning of a Serotype-specific A. pleuropneumoniae DNA region To identify and clone A. pleuropneumoniae J45 DNA involved in capsular polysaccharide biosynthesis, Southern blot analyses were performed to identify an adjacent DNA region upstream (in the 5' direction) from the cpxDCBA gene cluster involved in the export of capsule polysacharide described above (FIG. 10a–b and 11). It was expected this upstream DNA region would encode serotype-specific genes involved in capsular polysaccharide biosynthesis because the A.pleuropneumoniae capsulation (cap) locus seemed to be organized in a manner similar to the capsulation loci of Haemophilus influenzae type b and Neisseria meningitidis group B. BamHI-digested A. pleuropneumoniae J45 genomic DNA was probed with the digoxigenin-labeled 1.2 kb BamHI-Xbal fragment of pCW-1C that contained a portion of the cpxD gene. This cpxD-specific probe hybridized to a single, approximate 5.8 kb BamHI J45 genomic DNA fragment (data not shown). This 5.8 kb BamHI fragment was cloned into the BamHI site of pGEM-3Z from BamHI-digested J45 genomic DNA fragments in the range of 5.0–6.5 kb that were electroeluted (following electrophoretic separation) from an agarose gel. The resulting plasmid was designated pCW-11E and was restriction mapped (FIG. 1). A portion of the pCW-11E insert DNA (the 1.2 kb BamHI-Xbal fragment) overlapped the DNA present on the insert of pCW-1C.

Figure 2:
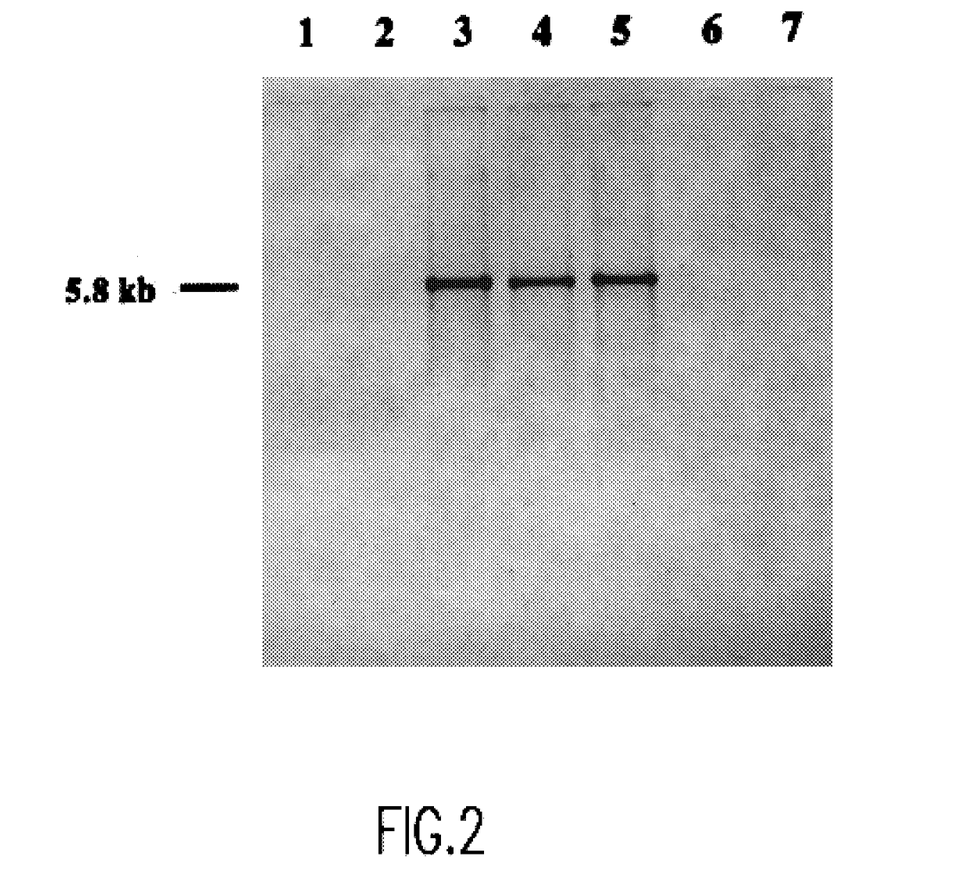

BamHI-digested genomic DNA from several different A. pleuropneumoniae serotypes was hybridized with the 2.1 kb Bglll-Stul fragment of pCW-11E (FIG. 1) to determine the serotype-specificity of this DNA region (FIG. 2). The 2.1 kb Bg/ll-Stul DNA fragment hybridized to a 5.8 kb BamHI genomic DNA fragment from three A. pleuropneumoniae serotype 5 strains tested, but not to genomic DNA from serotypes 1, 2, 7, and 9 (FIG. 2). Thus, the A. pleuropneumoniae DNA in pCW-11E contained DNA that was specific to serotype 5 strains. Because this DNA was serotype-specific, it was likely to be involved in capsular polysaccharide biosynthesis.

Nucleotide Sequence and Analysis of a Serotype-specific A. pleuropneumoniae DNA region The nucleotide sequence of the 2.7 kb Xbal-EcoRV DNA fragment of pCW-11E was determined. This nucleotide sequence was combined with the nucleotide sequence of the 4.6 kb Clal-Xbal fragment of pCW-11C and was examined for the presence of open reading frames (ORFs) not previously identified. The nucleotide sequence of the 3.2 kb Hinalll-EcoRV fragment of pCW-11E containing newly identified ORFs is provided in FIG. 3. Two complete ORFs, designated cpsA and cpsB (cps for capsular polysaccharide synthesis), were identified upstream and on the opposite strand from the cpxD gene involved in A. pleuropneumoniae capsular polysaccharide export (FIG. 1 and FIG. 3). The AUG initiation codon of cpsB was 3 nucleotides downstream from the UAA termination codon of cpsA. An AUG initiation codon of a third potential ORF, cpsC, was identified 15 bases downstream from the UAA termination codon of cpsB. Shine-Dalgamo ribosome-binding consensus sequences (Shine and Dalgamo, 1974) were identified within 13 bases upstream of the AUG initiation codons of cpsA, cpsB, and cpsC (FIG. 3). A putative promoter, containing sequences similar to the E. coli $^{70}$–10 (TATAAT) and –35 (TTGACA) consensus sequences (Hawley and McClure, 1983) was identified upstream of cpsA (FIG. 3). The close proximity of cpABC and the identification of a putative promoter upstream suggested that these ORFs may be co-transcribed. The G+C content for the DNA region encoding psABCwas 28%.

The predicted polypeptides of cpsA and cpsB were comprised of 321 (CpsA) and 526 (CpsB) amino acids (FIG. 3). The predicted molecular masses of CpsA and CpsB were 36.9 and 61.7 kiloDaltons (kDa), respectively. Hydropathy plots demonstrated that CpsA and CpsB were relatively hydrophilic proteins, suggesting that these proteins may be associated with the A. pleuropneumoniae cytoplasmic compartment (data not shown). BLAST searches (Altschul et al., 1990) of the combined, nonredundant nucleotide and protein databases at the National Center for Biotechnology Information did not reveal any substantial homology between cpsABC at the nucleotide or amino acid level with other sequences in the databases (data not shown). However, a low level of homology (15% similarity) was observed between CpsA and the E coli Rfb protein, an O-antigen glycosyltransferase involved in LPS biosynthesis (Cheah and Manning, 1993). A low level of homology (approximately 14% similarity) was detected between CpsB and the region 2 ORF 3 predicted protein product of the H. influenzae type b capsulation locus. The ORF 3 predicted protein is involved in the biosynthesis of the polyribosylribitol phosphate capsular polysaccharide of H. influenzae type b (Van Eldere et al., 1995). No significant homology was observed between the N-terminal 83 amino acids of CpsC and any proteins in the databases.

Figure 4:
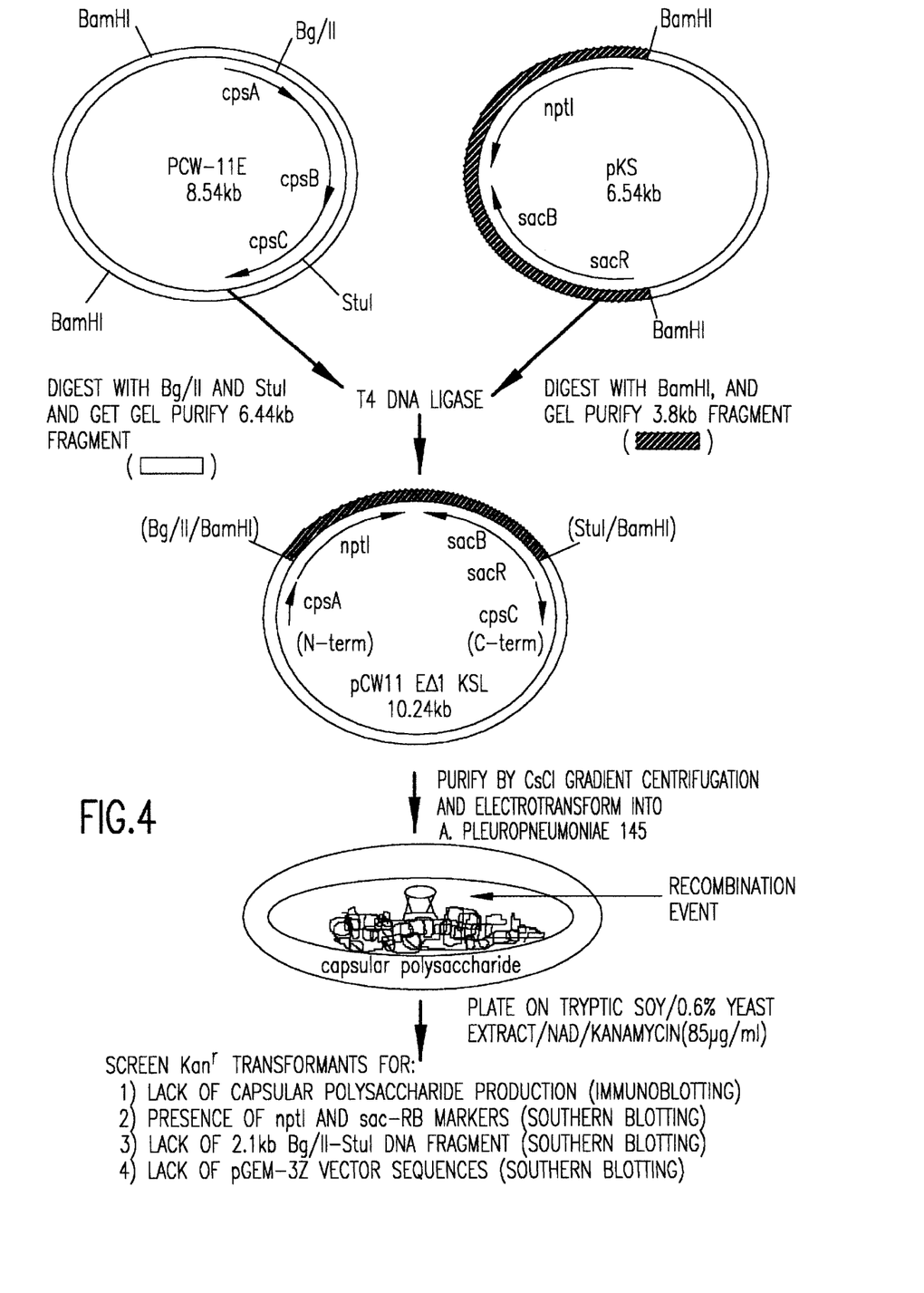
FIG. 4 describes construction of the suicide vector containing the deleted capsule synthesis DNA, pCW11EΔ1KS1, and production of noncapsulated mutants of *A. pleuropneumoniae* J45 by allelic exchange. The pCW11EΔ1KS1 plasmid vector was constructed by digesting pCW-11E with Bg/ll and StuI, making the ends blunt-ended, and ligating the large 6.4 kb fragment to the 3.8 kb BamHI fragment of pKS (also made bluntended) containing the nptl-sacRB (Kan$^r$ Suc$^s$) cartridge. Restriction sites in parentheses indicate the original ends of the fragments ligated in pCW11EΔ1KS1. The pCW11EΔ1KS1 vector was electrotransformed into *A. pleuropneumoniae*, and non-capsulated Kan$^r$ transformants were screened by lack of iridescence on media containing 85μg/ml of kanamycin.

Production of Kanamycin-resistant, Noncapsulated A. pleuropneumoniae Serotype 5a Transformants FIG. 4 schematically outlines the procedures used to produce recombinant, noncapsulated A. pleuropneumoniae J45 mutants by homologous recombination and allelic exchange. The vector pCW11EΔ1KS1 was first constructed to use as a nonreplicating, suicide vector to promote the exchange of wild type *A. pleuropneumoniae* capsulation DNA with genetically-altered *A. pleuropneumoniae* capsulation DNA by a double homologous recombination crossover event. The pCW11EΔ1KS1 vector was constructed by first digesting pCW-11E with Bg/ll and Stul to create a large deletion in serotype-specific *A. pleuropneumoniae* capsulation DNA. The ends of this digested DNA were made blunt ended, and the large 6.4 kb fragment was ligated to the 3.8 kb BamHI fragment of pKS (also made blunt ended) containing the nptl-sacR-sacB cartridge. This cartridge contains the Tn903 nptl gene before which is known to confer kanamycin resistance (Kan$^r$) to *A. pleuropneumoniae* (Tascon et al., 1994), and the sacRB sequences that confer sucrose sensitivity (Suc$^s$) to many gram-negative bacteria (Gay et al., 1983; Ried and Collmer, 1987). The deletion created in pCW11EΔ1KS1 spanned cpsABC (FIG. 1, FIG. 4) and was, therefore, likely to affect the protein products of these ORFs.

The pCW11EΔ1KS1 vector did not replicate in *A. pleuropneumoniae* and, therefore functioned as a suicide vector. After pCW11EΔ1KS1 was electroporated into *A. pleuropneumoniae* J45, seven kanamycin-resistant transformants were obtained after the recovery mixtures were incubated at 37° C. for 2 days. Four of these kanamycin resistant J45 transformants were noniridescent when visualized on plates with an obliquely transmitted light source, suggesting that these transformants were noncapsulated (data not shown). The medium used to grow *A. pleuropneumoniae* prior to electroporation with pCW11EΔ1KS1 was a factor since noncapsulated kanamycin-resistant transformants were never obtained when *A. pleuropneumoniae* was grown in brain heart infusion supplemented with NAD.

Genotypic Characterization of the Kanamycin-resistant *A. pleuropneumoniae* Transformants Preliminary colony hybridization analyses of the seven kanamycin-resistant transformants revealed that the four transformants which appeared noncapsulated (by visual inspection) hybridized with an nptl-specific DNA probe (the 1.24 kb Pstl fragment of pKS), but not with probes specific for pGEM-3Z (the 1.1 kb Bgll fragment pGEM-3Z) or the serotype-specific 2.1 kb Bg/ll-Stul fragment of pCW-11E (data not shown). These results indicated that a double recombination event had occurred in each of these four kanamycin-resistant transformants. In contrast, colonies of the other three kanamycin-resistant transformants hybridized to probes specific for the nptl gene, pGEM-3Z, and the 2.1 kb Bg/ll-Stul fragment of pCW-11E, suggesting that a single cross over had occured and the entire pCW11EΔ1KS1 suicide vector had integrated into the chromosome of these transformants (data not shown). Southern blot analyses of genomic DNA purified from the four kanamycin-resistant, potentially noncapsulated transformants (using the probes described above) were identical, indicating that the same double recombination event had occurred in each of these transformants. One of these transformants was randomly selected for further study and was designated J45-100.

Figure 5:
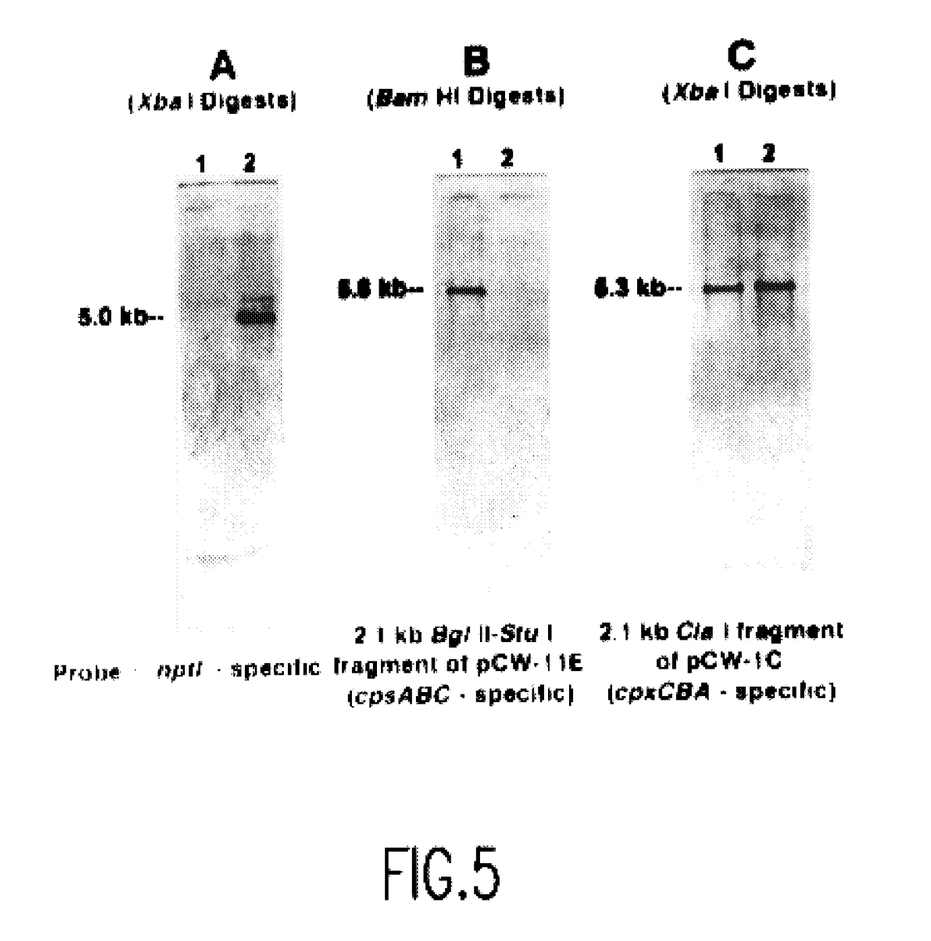
FIG. 5 is a southern blot analysis of genomic DNA isolated from *A. pleuropneumoniae* J45 (lane 1) or J45-100 (lane 2) with digoxigenin-labeled probes specific for nptl or portions of the *A. pleuropneumoniae* capsulation locus. *A. pleuropneumoniae* J45 (lane 1) or J45-100 (lane 2) genomic DNA was digested with XbaI (panels A and C) or BamHI (panel B), and hybridized with either the 1.24 kb PstI fragment of pKS (nptl-specific), panel A; the 2.1 kb Bg/ll-StuI fragment of pCW-11E (cpsABC-specific, see FIG. 1), panel B; or the 2.1 kb C/al fragment of pCW-1C (cpxCBA-specific, see FIG. 3.2), panel C.

Southern blot analyses of genomic DNA isolated from J45 and J45-100 with DNA probes specific for the nptl gene, the 2.1 kb Bglll-Stul fragment of pCW-11E, and the 2.1 kb Clal fragment of pCW-1C were performed (FIG. 5). The nptl-specific DNA probe hybridized to a 5.0 kb fragment of Xbaldigested J45-100 DNA, but not to J45 DNA, verifying that the nptl marker was in the chromosome of J45-100 (FIG. 5A). The hybridization of the nptl probe to a 5.0 kb Xbal J45-100 genomic DNA fragment was consistent with the size of this Xbal fragment in the pCW11E~1KS1 suicide vector used to produce J45-100. The 2.1 kb Bglll-Stul fragment of pCW-11E hybridized to a 5.8 kb fragment of BamHI-digested J45 but not to J45-100 DNA, verifying that this fragment was deleted in J45-100 (FIG. 5B). The probe specific for the cpxCBA genes (the 2.1 kb Clal fragment of pCW-1C) involved in capsular polysaccharide export hybridized to a 5.3 kb Xbal fragment of both J45 and J45-100 (FIG. 5C). This result verified that this portion of the *A. pleuropneumoniae* capsulation locus was unaffected by the double recombination event that had occurred within the adjacent DNA region. A probe specific for pGEM-3Z did not hybridize to genomic DNA from either J45 or J45-100, verifying that no vector DNA was contained in the genome of J45-100. Collectively, these DNA hybridization results indicated that the desired double recombination event and allelic exchange had occurred in J45-100.

Phenotypic Characterization of the *A. pleuropneumoniae* Kanamycin-resistant Transformant, J45-100

Figure 6:
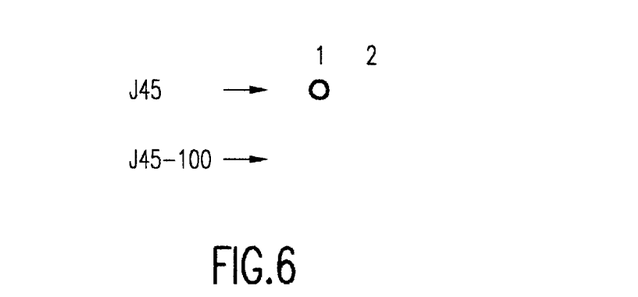
FIG. 6 is a colony immunoblot of *A. pleuropneumoniae* J45 and J45-100 reacted with a capsular polysaccharide specific swine antiserum. Approximately 5×10$^5$ (lane 1) or 5×10$^4$ (lane 2) CFU per well were applied to a nitrocellulose membrane. The membrane was lysed in chloroform and incubated with a swine antiserum that contained antibodies to the serotype 5a capsular polysaccharide but not other *A. pleuropneumoniae* surface antigens.

J45-100 was evaluated for capsular polysaccharide production by colony immunoblotting and latex agglutination. Antiserum containing antibodies specific for the *A. pleuropneumoniae* serotype 5a capsular polysaccharide, but not other bacterial surface components, reacted with J45 but did not react with J45-100 (FIG. 6). Because the bacterial colonies on the membrane had been lysed in chloroform, these results indicated that J45-100 did not produce intracellular or extracellular capsular polysaccharide. Whole or sonicated J45-100 did not agglutinate latex beads that were covalently conjugated to purified antibody to the serotype 5a capsular polysaccharide of *A. pleuropneumoniae* (Inzana, 1995), whereas J45 whole cells and sonicated J45-C cells strongly agglutinated the latex bead reagent (data not shown). These results verified that the deletion engineered into the cap locus of *A. pleuropneumoniae* J45-100 resulted in the loss of capsular polysaccharide biosynthesis. Furthermore, these results indicated that a noncapsulated mutant of J45 isolated after ethyl methanesulfonate mutagenesis (Inzana et al., 1993a), J45-C, produced intracellular but not extracellular capsular polysaccharide.

Figure 7:
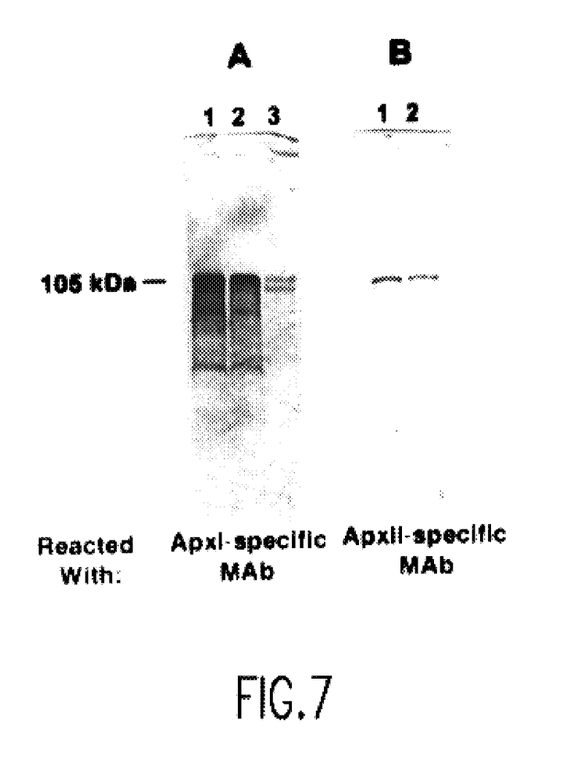
FIG. 7 shows immunoblots of *A. pleuropneumoniae* J45 (lane 1) and J45-100 (lane 2) concentrated culture supernatants containing predominately the exotoxins ApxI and ApxII. Panel A was reacted with an ApxI-specific monoclonal antibody, and panel B was reacted with an ApxII-specific monoclonal antibody. In panel A, the concentrated culture supernatant of *A. pleuropneumoniae* serotype 2 strain 1536 (lane 3) was included as a negative control because this serotype does not synthesize ApxI. The blot in panel A was reacted with the ApxI-specific monoclonal antibody.
Figure 8:
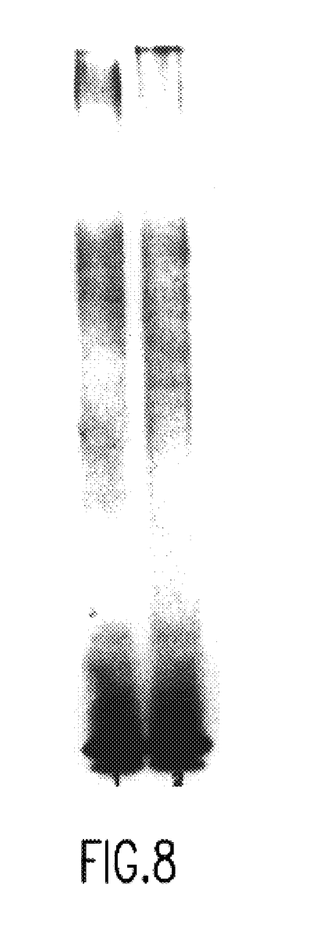
FIG. 8 shows the electrophoretic profiles of LPS isolated from *A. pleuropneumoniae* J45 (lane 1) and the recombinant noncapsulated mutant J45-100 (lane 2). LPS was electrophoresed through a 15% separating gel and stained with ammoniacal silver.

Apx toxin expression and the LPS electrophoretic profiles of J45 and J45-100 were compared to determine if the mutation engineered into the cap locus of J45-100 affected these important virulence determinants. No difference in secretion of the 105 kDa Apxl and Apxll toxin proteins into culture supernatant was detected between J45 and J45-100 (FIG. 7). In addition, no difference in the LPS electrophoretic profiles of J45 and J45100 was detected (FIG. 8).

Figure 9:
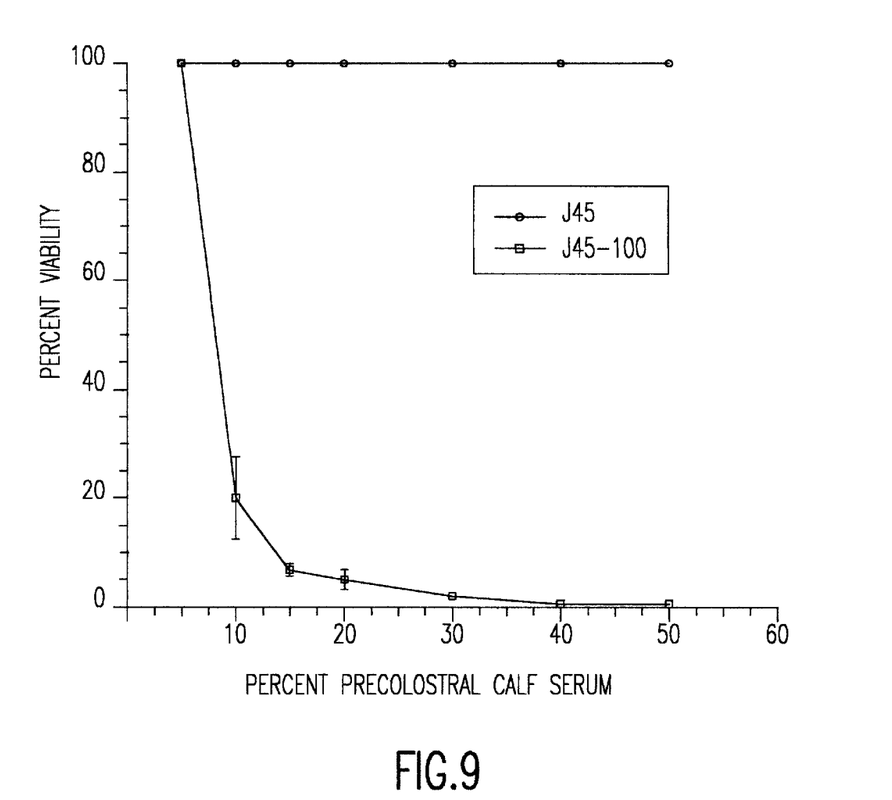

The growth of J45 and J45-100 in TSY-N and the sensitivity of J45 and J45-100 to the bactericidal activity of precolostral calf serum were examined to determine the effect of loss of encapsulation on these phenotypic properties. Growth curves of J45 and J45-100 in TSY-N were similar but not identical (data not shown). However, viable plate counts demonstrated that during the logarithmic phase of growth, J45-100 grew faster (generation time=ca. 23 minutes) than the parent encapsulated strain, J45 (generation time=ca. 28 minutes) (data not shown). The recombinant noncapsulated mutant, J45-100, was efficiently killed within 60 minutes in 10 to 50% precolostral calf serum as a complement source, whereas the encapsulated parent strain, J45, was not killed (FIG. 9).

The sucrose sensitivity of J45-100 was examined to determine whether the sacRB sequences could function as a counterselectable marker in *A. pleuropneumoniae* and subsequently induce the excision of the nptl-sacRB cartridge from the J45-100 chromosome. Broth-grown J45-100 grew very heavily when plated directly or when diluted and then plated on TSY-N or Luria-Bertani (to which 5 llg/ml NAD was added) medium containing 5% or 8% sucrose. The presence of the sacRB sequences in the chromosome of J45-100 was verified by Southern blotting. These results suggested that either the sacRB marker was not expressed in *A. pleuropneumoniae* or possibly that the levan product formed by the sacRB levansucrase in the presence of sucrose was not toxic to J45-100.

Intratracheal Challenge of Pigs with the Recombinant *A. pleuropneumoniae* Noncapsulated Mutant, J45100

The recombinant noncapsulated mutant, J45-100, did not cause any mortality in pigs when administered at doses 3 and 6 times ($1.45 \times 10^7$ CFU and $2.95 \times 10^7$ CFU, respectively) the 50% lethal dose (LD50) of the encapsulated parent strain, J45 ($5 \times 10^6$ CFU) (Inzana et al., 1993a) (Table 2). In contrast, all three of the pigs challenged with 6.5 times the $LD_{50}$ of J45 developed severe lung lesions and died (Table 2).

The non-capsulated strain of *Actinobacillus pleuropneumoniae* serotype 5 produced according to the above procedures only produces two of the three toxins made by *Actinobacillus pleuropneumoniae*. While the modified *Actinobacillus pleuropneumoniae* is protective and immunogenic, it may also be useful to clone the third RTX toxin gene into the deletion site.

This may be done by cloning the RTX toxin gene into the kanamycin gene cassette of strain J45-100, thus inactivating the kanamycin gene.

The vaccine should preferably be provided in a form similar to other vaccines well known in the art. It is preferable that the vaccine will be bottled as a lyophilized mixture, and can include one or more serotypes of mutant strains. To preserve viability, a substance such as Columbia broth, trehalose, or albumin, glycerol, or some other agent would be included. The contents of the lyophilized mixture would only need to be rehydrated with sterile water or saline

TABLE 2

Virulence of *A. pleuropneumoniae* J45 and J45-100 for pigs.

| Challenge Strain | Challenge Dose | Mean Lung Lesion Score | Number positive/total number tested | |
|---|---|---|---|---|
| | | | Mortality | Recovery[a] |
| J45 | $1.6–3.30 \times 10^{phu\ 7}$ CFU[b] | 4+ | 3/4[c] | 4/4 |
| J45-100 | $1.5 \times 10^7$ CFU | 0 | 0/5 | 0/5 |
| J45-100 | $3.0 \times 10^7$ CFU | 1+ | 0/5 | 2/5[d] |
| J45-100 | $8.4 \times 10^7$ CFU | 1+ | 1/4[e] | 4/4[b] |
| J45-100 | $1.8 \times 10^8$ CFU | 2+ | 0/4 | 4/4[d] |
| J45-C | $1.7 \times 10^8$ CFU | 1+ | 0/2 | 2/2[d] |

[a]Recovery of the challenge strain from lung samples taken at necropsy. Pigs challenged with J45-100 were necropsied 4 days post-challenge.
[b]This dose is 6.6 times the 50% lethal dose ($5 \times 10^6$ CFU) reported in a previous study (Inzana et al., 993a).
[c]All of the pigs in this group died within 36 hours post-challenge.
[d]*A. pleuropneumoniae* was recovered from the lungs, and was confirmed to be noncapsulated by lack of iridescence and failure to agglutinate serotype 5-specific sensitized latex particles.
[e]Necropsy of the one pig that died indicated that death was due to mis-administration of challenge dose.

The five pigs challenged with the lower dose of J45-100 ($1.45 \times 10^7$ CFU) did not exhibit any clinical symptoms characteristic of swine pleuropneumonia and did not develop any lung lesions. Furthermore, *A. pleuropneumoniae* was not cultured from lung samples taken four days post-challenge at necropsy. Two of the five pigs challenged with the higher dose of J45-100 ($2.95 \times 10^7$ CFU) were clinically normal and no lung lesions were observed at necropsy. One pig in this group challenged with the higher J45-100 dose exhibited moderate dyspnea, and at necropsy some lung congestion and slight hemorrhage were observed (lung lesion score=1+). The remaining two pigs in this group exhibited mild dyspnea, and at necropsy some pleuritis and consolidation were observed (lung lesion score=2+). *A. pleuropneumoniae* J45-100 was cultured only from these two pigs. with the most severe lung lesions. The bacteria recovered from these pigs did not agglutinate the serotype 5a latex bead agglutination reagent. Thus, the recovered bacteria were still noncapsulated, indicating that J45-100 did not revert to the encapsulated phenotype in vivo.

While nptI (confers resistance to kanamycin) and SacB/ SacR (confers sensitivity to sucrose) genes were cloned into the deletion site, these genes were only intended to be used as marker genes. Alternative marker genes may also be employed. It may be preferable to avoid using an antibiotic resistant marker such as nptI for health and safety related reasons, or to provide a mechanism for curing or inactivating the antibiotic marker. Suitable non-antibiotic markers might include mercury resistance.

and injected (intramuscular, intravenous, intraperitoneal, subcutaneous, etc.). The vaccine may also be formulated for other modes of administration as well (e.g., oral, transdermal, sublingual, etc.) using appropriate carrier matrixes (e.g., starch, polsaccharides, oils, liposomes, gums, etc.).

The dose of the vaccine provided to an animal will depend on such factors as the age or sex of the animal, and the mode of delivery. In all cases, a sufficient quantity of the live, a virulent, non-capsulated *Actinobacillus pleuropneumoniae* should be provided to give rise to an immunogenic response in the vaccinated animal. Successful results have been obtained with 2 immunizations 2 to 3 weeks apart of $10^9$ colony forming units.

While the invention has been described in terms of its preferred embodiments, those skilled in the art will recognize that the invention can be practiced with modification within the spirit and scope of the appended claims.

We claim:

1. A vaccine comprised of an avirulent, non-capsulated *Actinobacillus pleuropneumoniae* bacteriuln, said bacteriun lacking DNA capsule synthesis sequences coding for capsule synthesis, said sequences being located upstream from a hybridization site for a BamHI-XbaI fragment of pCW-1C.

2. A method of immunizing swine against pleuropneumoria, comprising the step of administering to said swine an immunogenic dose of a vaccine comprising an avirulent, non-capsulated *Actinobacillus pleuropneumoniae* bacterium which lacks DNA capsule synthesis sequences coding for capsule synthesis, said sequences being located upstream from a hybridization site for a BamHI-XbaI fragment of pCW-1C.

3. A method of preparing a vaccine to prevent diseases caused by *Actinobacillus pleuropneumoniae*, comprising the steps of:

identifying DNA capsule synthesis sequences coding for capsule synthesis in said bacteria, said DNA capsule synthesis sequences being located upstream from a hybridization site for a BamHI-XbaI fragment of pCW-1C; and deleting said DNA capsule synthesis sequences to produce non-capsulated mutants of said bacteria.

4. A vaccine comprised of an avirulent, non-capsulated *Actinobacillus pleuropneumoniae* bacterium, said bacterium lacking DNA capsule synthesis sequences coding for capsule synthesis, said sequences being located upstream from a capsular export gene of said bacterium.

5. The vaccine of claim 4 wherein said capsular export gene is cpxD.

* * * * *